(12) United States Patent
Rosario et al.

(10) Patent No.: US 7,496,995 B2
(45) Date of Patent: Mar. 3, 2009

(54) CONTAINMENT DEVICE

(76) Inventors: Adamo Rosario, Unit 6, 10 Oriele Street, Perigian, Queensland (AU) 4576; Michael Edmond Petrascu, 7 Mirrabook Court, Noosa Heads, Queensland (AU) 4567

( * ) Notice: Subject to any disclaimer, the term of this patent is extended or adjusted under 35 U.S.C. 154(b) by 276 days.

(21) Appl. No.: 11/455,290

(22) Filed: Jun. 15, 2006

(65) Prior Publication Data
US 2007/0009187 A1    Jan. 11, 2007

Related U.S. Application Data

(63) Continuation of application No. PCT/AU2004/001752, filed on Dec. 13, 2004.

(30) Foreign Application Priority Data
Dec. 16, 2003    (AU)    ............................. 2003906939

(51) Int. Cl.
*A61G 1/00* (2006.01)

(52) U.S. Cl. ........................ 27/28; 383/103; 220/89.1

(58) Field of Classification Search ............... 27/28, 27/11, 7; 383/103, 100, 94; 220/89.1; 206/524.8
See application file for complete search history.

(56) References Cited

U.S. PATENT DOCUMENTS

| | | | | |
|---|---|---|---|---|
| 4,122,993 A * | 10/1978 | Glas | ............................. | 383/103 |
| 4,134,535 A * | 1/1979 | Barthels et al. | ............. | 383/102 |
| 4,583,643 A * | 4/1986 | Sanderson | ................... | 206/438 |
| 4,790,051 A * | 12/1988 | Knight | ........................... | 27/28 |
| 5,584,409 A * | 12/1996 | Chemberlen | ............... | 220/89.1 |
| 5,659,933 A * | 8/1997 | McWilliams | ................... | 27/28 |
| 5,893,461 A * | 4/1999 | Walters | .................... | 206/524.8 |
| 6,004,034 A * | 12/1999 | Salam | .......................... | 383/66 |
| 6,056,439 A * | 5/2000 | Graham | ...................... | 383/103 |
| 6,070,728 A * | 6/2000 | Overby et al. | ............ | 206/524.8 |
| 6,663,284 B2 * | 12/2003 | Buckingham et al. | ....... | 383/103 |
| 6,953,148 B2 * | 10/2005 | Esakov et al. | ................. | 232/30 |
| 7,228,603 B2 * | 6/2007 | Craig | ............................ | 27/28 |
| 7,337,511 B2 * | 3/2008 | Yu et al. | ......................... | 27/28 |
| 2003/0035597 A1 * | 2/2003 | Buckingham et al. | ....... | 383/103 |

FOREIGN PATENT DOCUMENTS

| | | |
|---|---|---|
| FR | 2549737 | 2/1985 |
| FR | 2569345 | 2/1986 |
| FR | 2717678 | 9/1995 |
| WO | WO 2002/074217 | 9/2002 |

* cited by examiner

*Primary Examiner*—William L. Miller
(74) *Attorney, Agent, or Firm*—Young & Thompson

(57) ABSTRACT

A bag device for storing a body includes upper and lower impervious flexible panel members each having opposed side edges and opposed ends. Respectively side edges of the members are formed integrally therealong, and the members are movable to form a cavity for storing the body. The end is closed and the end is normally open so that can be inserted into the cavity. The members are laminates of thermoplastic sheets and the open end can be sealed by application of heat to the thermoplastic sheets at the open end. Pressure release valves are fixed to the member so that excess pressure in the cavity due to body decomposition is released to the atmosphere.

39 Claims, 4 Drawing Sheets

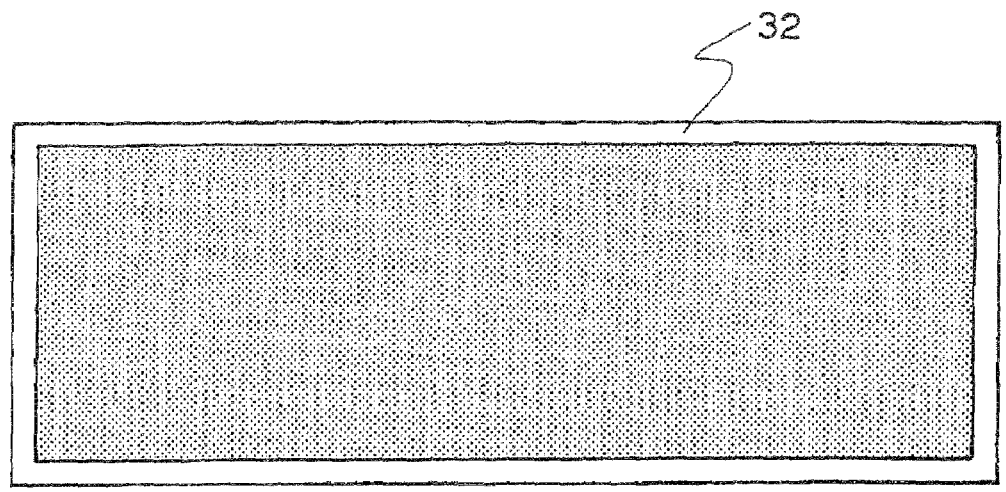
Fig_3_
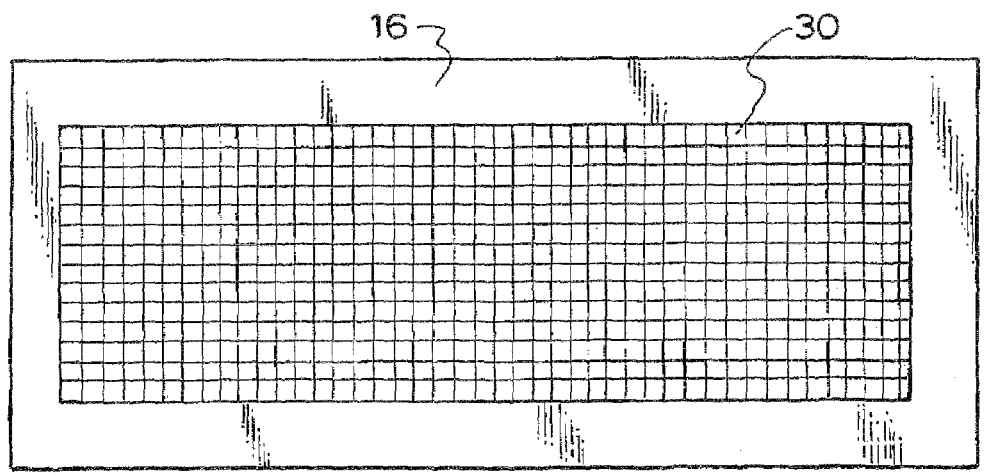
Fig_4_

CONTAINMENT DEVICE

BACKGROUND OF THE INVENTION

Bodies and body remains of dead human beings and animals tend to decompose in a relatively short time. When left uncovered, the bodies and body remains that carry diseases or viruses will spread through either a direct contact therewith, or an indirect transfer by insects or other human beings or animals which have become infected with the diseases or viruses. Some of the diseases or viruses can also be carried by a flowable medium such as air or water, and therefore can be spread by air or water.

Decomposition of the bodies and body remains commences well before burial or cremation. The decomposition process produces liquid and gaseous products which have unpleasant odours. The decomposition products may find their way to an underground stream, a river or a water resource that is used by nearby inhabitant. Any escape of the liquid decomposition products can cause serious health problem to the general community.

The unpleasant odours are especially prevalent in days of relatively high temperature. In addition, at that time many more insects are attracted by the odours and they help to spread diseases or viruses.

People managing mausoleums or burial sites have made many attempts to minimise effects due to the decomposition products. Examples of these attempts include embalming bodies, treatment with preservatives and sealing coffins. The process of embalming bodies is time consuming and it has a limited effect in containing decomposition products. The preservatives may be toxic, and as such people managing the burial sites must take steps to prevent leakage of the preservatives into the environment. Totally sealing a coffin is costly and there is a danger of explosion due to the decomposition products building up of pressure therein. In some cases, mausoleum management uses metal trays in coffins to retain the liquid decomposition products, and a venting system to force the gaseous decomposition products into atmosphere. Deodorising agents and other chemicals have also been used to disguise the unpleasant odours for a short time period.

Disposal of the liquid and gaseous decomposition products in mausoleums is therefore difficult. It is also difficult to prevent leakage of these products from mausoleums.

For bodies and body remains that are to be subject to analysis, any loss or contamination of the body remains may seriously affect results of the analysis. Embalming or treatment with preservative can also affect accuracy of an analysis of a body remain. This is undesirable, especially in an autopsy when the cause or causes of death need to be correctly determined. The loss of fluids in or parts of or contaminations of bodies or body remains may also spread infectious diseases.

OBJECT OF THE INVENTION

It is an object of this invention to provide a containment device which alleviates or reduces to a certain level one or more of the above problems.

SUMMARY OF THE INVENTION

As used hereinafter, the word "body" is taken to mean a body or body remain of a dead person or animal.

In one broad aspect therefore the present invention resides in a containment device for storing a body. The containment device includes a substantially elongate upper impervious flexible panel member and a substantially elongate lower impervious flexible panel member, and the upper and lower panel members each having an inside surface, an outside surface, opposed side edges and opposed ends. Respective side edges of the upper and lower panel members are sealingly joined together or formed integrally therealong, and the upper and lower panel members are movable relative to each other to form a cavity between the inside surfaces. The opposed ends form respective ends of the device and at least one of the device ends is openable so that through the or one of the open end(s) the body can be inserted into the cavity for storage. A sealing arrangement is arranged for sealingly closing the or one of the open end(s) by application of heat and/or pressure, whereby the cavity is hermetically sealed. The device further includes a fluid absorbent composition arranged on the inside surface of said lower panel member for absorbing gaseous and/or liquid decomposition products escaping from said body, and at least one pressure release means arranged through an aperture in said upper panel member for releasing pressure in the cavity when the pressure due to the gaseous and/or liquid decomposition products in the cavity exceeds a predetermined level. Said at least one pressure release means has a first housing member configured with a first chamber therein and a second housing member configured with a second chamber therein. Said first housing member is arranged within the cavity and said second housing member is arranged on said outside surface of the upper panel member. A pressure sensitive valve member is positioned between the first and second chambers and is arranged to open to allow the gaseous decomposition products to pass into the second chamber and through vents in said second housing member to atmosphere and thereby releasing pressure in the cavity when the pressure therein exceeds said predetermined level. Said first chamber contains vapour retention media for substantially retaining vapour entrained in the gaseous decomposition products and said second chamber contains bacteria filtering media for substantially filtering bacteria before the filtered gaseous decomposition products passing through said vents.

The or one of said at least one pressure release means may be arranged for connection to evacuation means for evacuating air within the cavity following sealing thereof. Preferably, the valve member is housed within a collar extending from said first housing member. The collar is adapted for connection to said evacuation means and said second housing member is configured for removably securing to said collar and is removable therefrom to provide access to connect the evacuation means to the collar for evacuating the cavity.

It is preferred that air conditioning media are also provided in one or both of said first and second chambers.

One or more hand grips may be formed along each of the side edges. Preferably, the handgrips are each reinforced with a PVC tubing. More preferably, each handgrip is in the form of a cutout section in one of said side edges and the PVC tubing is fixed in said cutout.

In preference, each of said upper and lower panel members is formed by lamination or co-extrusion of one or more layers of material or materials. It is further preferred that each of said upper and lower panel members has at least one layer of an impervious metallic film(s) and at least one layer of a polymeric material(s). Each of said upper and lower panel members may be arranged so that the at least one layer of a metallic film(s) is between an outer one and an inner one of the at least one layer of a polymeric material(s). Preferably, said outer layer is relatively more tear and/or puncture resistant than said inner layer. In one form, the polymeric material for said outer layer is nylon or polycarbonate, and the polymeric material for said inner layer is polyethylene.

More preferably, said one or more layers of material or materials include at least one layer of ethylene vinyl alcohol bonded to the or each of said at least one layer of a metallic film(s). The at least one layer of a metallic film(s) may be an aluminium foil(s). The at least one layer of ethylene vinyl alcohol not only facilitates bonding of the at least one layer of a metallic film(s), it also assists in absorbing methane which is one of the decomposition products.

The sealing arrangement may be in the form of a heat and/or pressure sealable material arranged on the inside surface of one each of the upper and lower panel members in a position at or adjacent to said at least one open end. In one form the pressure sealable material is a strip of silicon. The heat sealable material can be a strip of heat weldable material such as thermoplastic. More preferably, at least the panel member(s) or the layer of the panel member(s) having said inside surface, is formed of a heat weldable material so that a simple application of heat within a predetermined range of temperature will form a weld joint between the panel members and thereby sealing the cavity.

Preferably the at least one opening is arranged at one end of the device. The other end of the device may be open or closed. If it is normally open then the sealing arrangement as hereinbefore described is also provided for sealing said other end.

One or more gas evacuation means can be provided for evacuating gases in the containment device following sealing of the at least one opening. Alternatively the at least one pressure release means can be arranged to evacuate gases and to release pressure when pressure inside the cavity exceeds said predetermined level.

Evacuation of gases in the containment device slows down the decomposition process. Accordingly the time for decomposition gas products to build up to the pressure level at which the one or more pressure release means will react to release pressure is much longer. The evacuation also lowers the oxygen level in the bag. The lowered oxygen level helps to reduce the risk of spontaneous combustion that can result from a high ratio of oxygen and combustible decomposition gases.

Typically said absorbent composition is arranged on the inside surface of said lower panel member or contained in one or more packages arranged on the inside surface of said lower panel member. The absorbent composition arranged on the insider surface of said lower panel member or contained in the one or more packages may be covered with a pliable perforated sheet attached to said inside surface. Preferably, said perforated sheet is formed of a polymeric material such as polyethylene.

It is preferred that the fluid absorbent composition includes one or more liquid absorbent materials arranged for absorbing liquid decomposition products from said body. Said one or more liquid absorbent materials are preferable selected from any one or more of silica gel, calcium chloride and sodium polyacrylate. Typically, said fluid absorbent composition includes a mixture of silica gel, calcium chloride and sodium polyacrylate. In the mixture, the silica gel may be up to 30%, the calcium chloride up to 8% and the sodium polyacrylate up to 80%. It is further preferred that the fluid absorbent composition includes one or more gaseous absorbent materials arranged for absorbing gaseous decomposition products. Said one or more gaseous absorbent materials preferable contains activated carbon.

Preferably, said vapour retention media are in the form of a mixture of clay and calcium chloride and the retention mixture is arranged to provide a retention capacity of between 15% to 35% by weight. More preferably, the retention capacity is 20% to 30% by weight. In a specific form, the retention mixture has a mesh size of 8×12 mesh (approximately 1.5-2.6 mm) and a pore size of 10 Angstrom ($10 \times 10^{10}$ mm). Calcium chloride is also a preservative material so that any fluid absorbed into this material can be preserved for a relatively longer time.

Said air conditioning media may include petroleum based activated carbon and/or fibre based activated carbon. The air conditioning media may also include sodium polyacrylate. Said petroleum based activated carbon and/or fibre based activated carbon, and sodium polyacrylate, where included, may be arranged in layers or a mixed mass. In one application, the petroleum based activated carbon is in the form of a layer between 20 to 40 mm, and the fibre based activated carbon is in the form of a layer between 20 to 40 mm, and sodium polyacrylate, where included, is in the form of a layer between 5 to 15 mm.

The bacteria filter is arranged to filter out the majority of known bacteria in a decomposing body remains so as make the treated air that is released back into the environment substantially non hazardous. Accordingly, the filtering of bacteria provides a safer environment for cemetery and mausoleum workers in respect of bacterial contamination. The bacteria filtering also limits bacteria contamination to other workers in different types of applications, e.g. field workers in natural and man-made disaster situations where there are multiple deaths, vets and farmers where there are animal deaths.

The bacterial filter is typically in the form of a mixture of paper fibers and glass fibers and is manufactured to a weight of approximately 80 grams/meter 5. This will produce a very small pore size and according to a HOT DOP testing to AS 1324 standard test will only let pass 0.014% of all particles that are less than 0.3 microns. This figure of 0.3 microns is very significant as it is widely regarded as the lowest particle size for bacteria, *rickettsiae* and fungi and most pathogens.

The bacteria filter may be arranged in a concertina shape to increase filter per unit area so it lessens the chance of a pressure build up. Preferably, the bacteria filter has at least one flat circular shaped bacterial filter element.

Absorption of the liquid and gaseous decomposition products as they are formed also helps to reduce pressure in the containment device. In the case of hydrogen sulfide produced during decomposition the absorption process helps to disproportionate it to other compounds that have no odour in the liquid phase.

The composition materials substantially absorb the liquid and gaseous decomposition products, and minimise foul odours.

The absorbent materials also help to lower microbial activity of bacteria and fungi usually associated with decomposition. This is apparently influenced by the reduction in available water and/or water vapour which are important conditions for bacterial and fungal growth. Bacterial and fungal activities are also inhibited in the presence of terpene compounds on the active surfaces of the absorbents and in the air space about them.

The containment device of the present invention can also be used within a coffin. Accordingly there is no need to modify or purchase specially designed coffins in attempting to overcome the prior art problems. Mausoleums and other funeral houses can therefore use the containment device as a very cost effective way to solve the prior art problems.

In another aspect thereof the present invention relates to a body containment system including a plurality of containment devices formed as a linear array, the array being arranged so that the devices are folded into a stack or rolled in a roll, and the bags being separable along joints between adjacent bags, each of said devices being the containment device substantially as hereinbefore described, and heating and/or pressure means have spaced heating and/or pressure elements having a length which is equal to or greater than the width between the opposed side edges of a containment device. At least one of the heating and/or pressure elements is movable towards the other heating and/or pressure element. In use, a containment device is separated from the stack or roll, and placed with said at least one open end thereof between the heating and/or pressure elements and the sealing arrangement in alignment therewith. The movable heating and/or pressure element is then moved towards the other heating and/or pressure element so that the containment device is in contact with the heating and/or pressure elements and the sealing arrangement is being heated and/or pressured by the heating and/or pressure elements. The heat and/or pressure applied causes the sealing arrangement to form a weld joint and thereby sealing the cavity. The movable heating and/or pressure element then can be moved so that the containment device can be released from the heating and/or pressure means.

The heating and/or pressure means may have a base and spaced posts extending from the base. The heating and/or pressure elements are arranged on the posts with the movable element above the other element. Preferably, a handle is fixed to the movable element so that movable element can be moved as the handle is moved along the posts.

BRIEF DESCRIPTION OF THE INVENTION

In order that the present invention can be more readily understood and be put into practical effect reference will now be made to the accompanying drawings which illustrate one preferred embodiment of the invention and wherein:

FIG. 3 is a longitudinal section view of the containment device shown in FIG. 2;

FIG. 4 is a view of the containment device shown in FIG. 2 with the perforated layer removed;

DETAILED DESCRIPTION OF THE INVENTION

Figure 1:
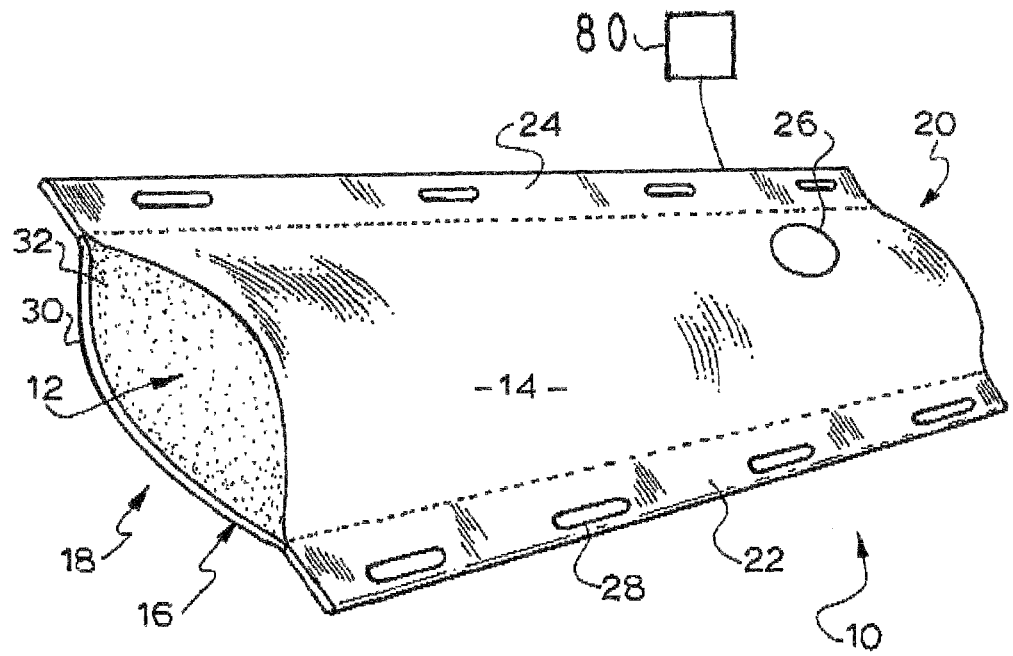
FIG. 1 is a perspective view of a schematic body containment device according to one embodiment of the present invention.

Referring to the drawings and initially to FIG. 1 there is shown a body containment device 10 for containing a body (not shown) in a cavity 12 thereof and the device 10 is to be used for hermetically sealing the body before subjecting the body to an analysis such as autopsy or for use in a mausoleum before burial or cremation.

Figure 2:
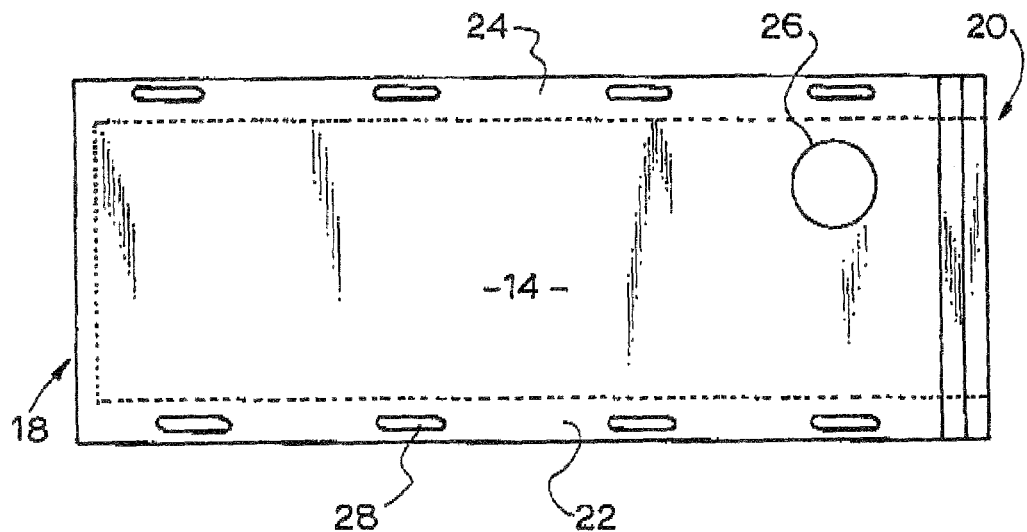
FIG. 2 is a top view of a schematic body containment device according to another embodiment of the present invention.

The containment device 10 has an upper impervious flexible panel member 14, a lower impervious flexible panel member 16 arranged opposite to the top panel member 14, ends 18 and 20, and edges 22 and 24. The panel members 14 and 16 are laminated sheets co-extruded from layers of polymeric materials such as a polyethylene and nylon, and one or more layers metallic foils such as an aluminium foil bonded to layers of ethylene vinyl alcohol. In this embodiment the opposed edges 22 and 24 of the panels members 14 and 16 are weld joined together. Theses edges may be integrally formed in some cases. In this embodiment the ends 18 and 20 are open and they can be sealed following insertion of a body from either end into the cavity 12. In the FIG. 2 embodiment, the end 18 is heat sealed to form a closed end. The end 20 is open so that in use a body (not shown) can be inserted into the cavity 12. The open end 20 is heat sealed following insertion of the body. The containment bag device 10 is then hermetically sealed.

The top panel member 14 has a pressure sensitive one way pressure release valve 26 which is set to release gases built up within the cavity 12 when the pressure therein is over a predetermined level.

The valve 26 can be connected to a vacuum pump (not shown) to evacuate air and other gases in the cavity 12 following sealing of the end 20. The cavity 12 then is a partial vacuum.

Arranged along each of the welded edges 22 and 24 are four hand grips 28. Each of the hand grips 20 are formed with an aligned cutout through the opposed edges and a plastic grip ring positioned therein.

Applied to the inside surface of the lower panel member 16 is a mixture of fluid absorbent materials 30 below a perforated layer 32 of polyethylene (also see FIGS. 3 and 4). The absorbent materials are selected to absorb liquid and gaseous decomposition products from a body remain to be placed in the cavity 12 and on the layer 32.

In this embodiment, the absorbent materials for the mixture 30 consist of about 20% of silica gel, about 5% of calcium chloride, about 5% of activated carbon, and the rest is slightly cross-linked sodium polyacrylate. A small amount (about 2%) of vapour retention materials such as a mixture of clay and calcium chloride is also added to the absorbent mixture 30.

Figure 5:
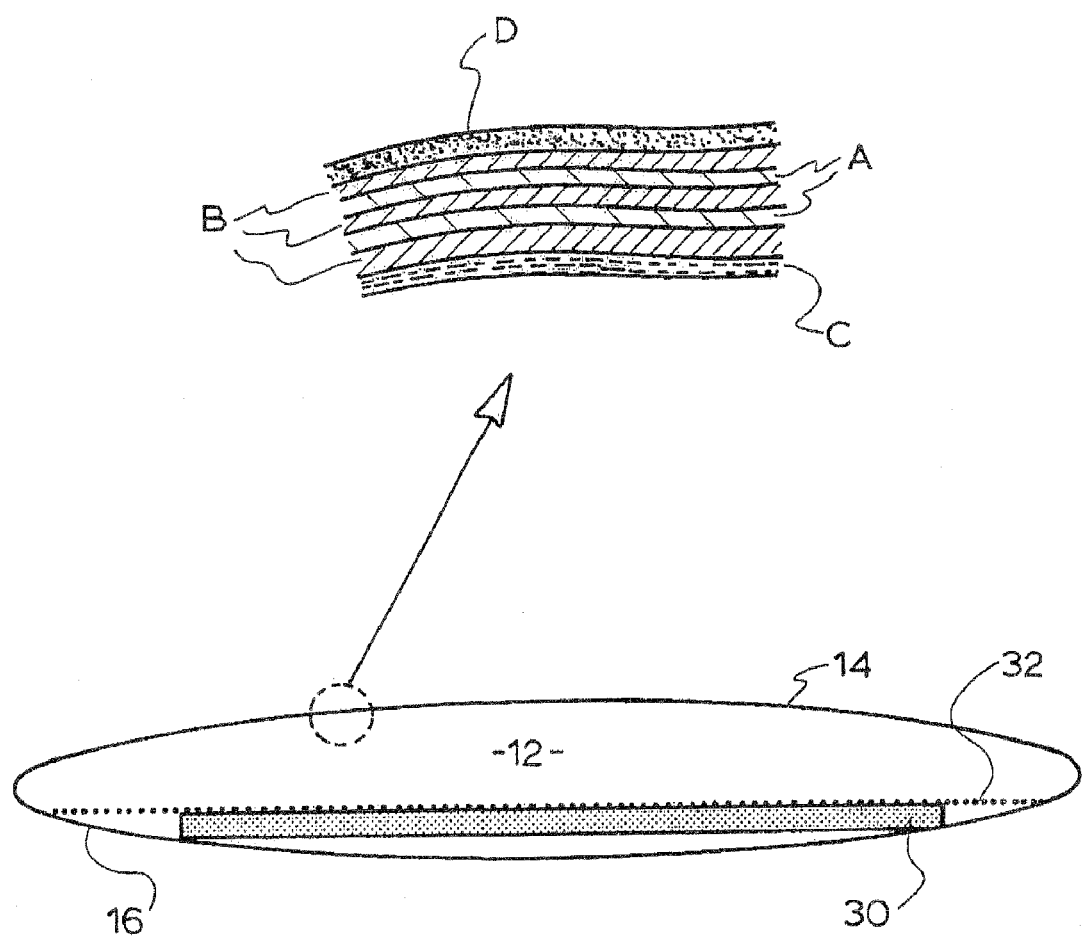
FIG. 5 is a cross-sectional view of the containment device shown in FIG. 2.

Turning to FIG. 5, each of the upper and lower panel members 14 and 16 have two layers of aluminium foil A sandwiched between and bonded to layers of ethylene vinyl alcohol B. Ethylene vinyl alcohol not only has the property of bonding to aluminium foil, it also absorbs some methane within the gaseous decomposition products. The aluminium foils prevent the decomposition products from seeping through the panel members into the atmosphere.

The inner most layer C is linear low density polyethylene so that the end 20 and/or the end 18 can be sealed by welding when the inside surfaces of the upper and lower panel members 14 and 16 are brought together with the application of heat thereat. The top layer D is nylon which is substantially tear and impact resistant so that the aluminium foils are protected from damage during normal use of the containment device 10.

Figure 6:
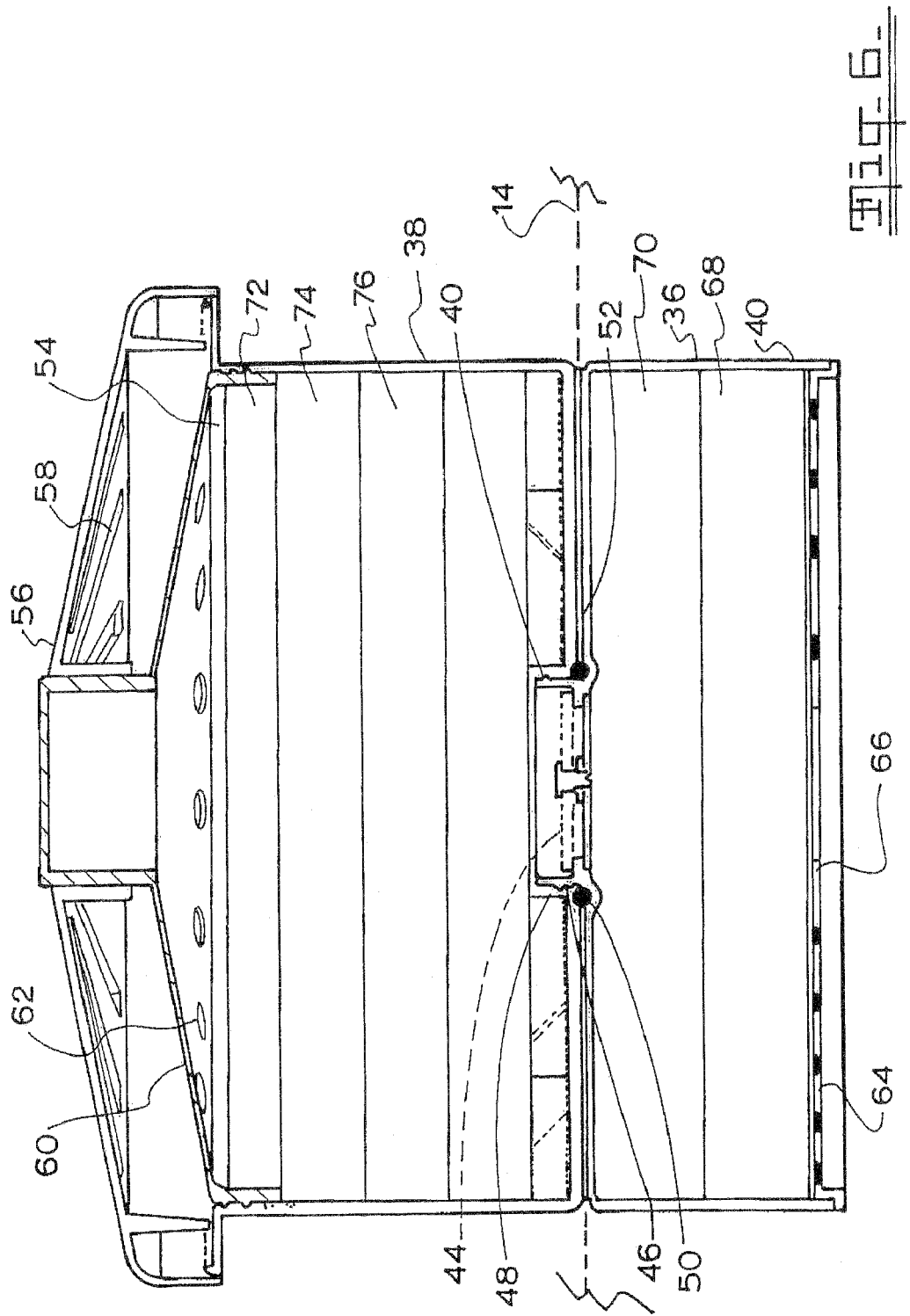
FIG. 6 is a cross-sectional view of an embodiment of the pressure relief valve shown in FIGS. 1 and 2.

FIG. 6 shows details of the pressure sensitive one way pressure release valve 26. The valve 26 in this embodiment has a first housing member 36 arranged positioned within the cavity 12, and a second housing member 38. The first housing member 36 has a first chamber 40 therein and a collar 42 for accommodating a one way valve member 44. The collar 42 extends through an opening 46 in said upper panel member 14 and is configured for removable coupling to said second housing member 38. In this regard, the collar 42 has external screw threads arranged to cooperate with internal screw threads of a sleeve 48 in said second housing member 38. A compressible sealing ring 50 is positioned around the collar 42 for preventing air from escaping between the collar 42 and the sleeve 48. A rubber washer 52 is also provided to close any air passage scaping between the first housing member 36 and the upper panel member 14. The second housing member 38 has an open top 54 closed by a cap 56 with elongated vents 58. A sealing diaphragm 60 with vent holes 62 is fixed to the cap 56 so that gases passing through the second housing member 38 are directed through the vent holes 62 and the elongated vents 58 into the atmosphere.

The first chamber 40 contains vapour retention media 68 for substantially retaining vapour entrained in the gaseous decomposition products entering into the chamber 40 through a number of vents 64 in a base 66 of the first housing member 36. Air conditioning media 70 is also arranged in the first chamber 40 for trapping relatively large particles in the gaseous decomposition products. The vapour retention media in this embodiment are in the form of a vapour sieve consisting of a mixture of clay and calcium chloride. This vapour sieve has the following properties:

| | |
|---|---|
| Mesh size: | 8 × 12 mesh (approximately 1.5-2.6 mm) |
| Pore size: | 10 Angstrom ($10 \times 10^{-10}$) |
| Absorption capacity: | 24.2% (by weight) |

The air conditioning media 70 in this embodiment is activated carbon.

It should be noted that while the vapour filtering media 68 and the air conditioning media 70 as shown are in stacked layers, they can be co-mingled as a mass within the first chamber 40.

The second chamber 54 as shown contains bacteria filtering media 72 for substantially filtering bacteria before the filtered gaseous decomposition products passing through said vents 62 and 56 in the second housing member 38. The chamber 54 in this embodiment also has three layers of air conditioning media 74, 76 and 78. For this embodiment, the media 74 are petroleum based activated carbon, the media 76 are activated carbon fro coconut fibres and the media 78 are sodium polyacrylate. The layers of media 74, 76 and 78 can be stacked in any order. Further, the media 74, 76 and 78 and the bacteria filtering media can be co-mingled as a mass.

In use, a containment device 10 is separated from a roll of linearly connected containment devices and the unsealed end 18 is opened for insertion of a body into the cavity 12 of the separated containment device 10. The open end 18 of the separated containment device 10 is then sealed by application of heat and/or pressure. The pressure release means 26 is then connected evacuation means such as a vacuum cleaner 80 for evacuating air within the cavity 12. In this regard, the second housing member is unscrewed for removal from the collar 42 and the hose of the vacuum cleaner is connected to the collar 42 for drawing air within the cavity 12 through the valve member 44. Thereafter, the second housing member 38 is again fixed to the collar 42.

While the containment device 10 described in above embodiment is for containing a single body it should be noted the device 10 of present invention can be adapted for containing more than one body.

Tests have shown that the panel members 14 and 16 are strong and durable. The panel members 14 and 16 have the following properties:

| | Material | | |
|---|---|---|---|
| Structure: | A co extruded film with layers of linear low-density polyethylene, nylon, and ethylene vinyl alcohol. Two Aluminium layer bonded between layers of polyethylene, nylon and ethylene vinyl alcohol | | |
| Made Form: | Rolls of lay flat tubing or sheets | | |
| Colour: | Natural (tinted colours may be an option) | | |
| Film Thickness: | 200 microns | | |
| Film Width: | made at 770 mm though 1000 mm will be the final requirement | | |
| Length | Continuous up to 800 m long | | |
| Tensile Properties: | Yield Strength | MD | 22.1 Mpa |
| | | TD | 21.2 MPa |
| | Break Strength | MD | 28.8 Mpa |
| | | | 23.9 MPa |
| | Elongation at Break | MD | 330% |
| | | TD | 280% |
| Tear Strength | MD | 4.5 N | |
| | TD | 6.6 | |
| Haze: | 37% | | |
| Puncture Resistance: | 2.1 N | | |
| Impact Strength: | >600 g | | |
| Odour Barrier: | To dihydrogen sulphide:- No detectable odours in free standing packs. In enclosed packs at 23° C., no odour after 24 hours. In enclosed packs at 40° C. for 7 days, an unpleasant odour in head space but not strong. | | |
| Oxygen Barrier: | <1.5 cc/m$^2$/24 hr/atm at 23° C., 75% rh | | |
| Chemical Resistance: | No detectable change in material when exposed to a mixture of hydrogen sulphide gas, water and dilute hydrochloric acid, for 7 days at 40° C. | | |
| Moisture Barrier: | <3 g/m$^2$/24 hrs at 38° C., 90% rh | | |
| Trial Status Property Claim: | All properties are indicative values and should not be taken as limiting specifications | | |
| Odour Barrier: | To dihydrogen sulphide:- No detectable odours in free standing packs. In enclosed packs at 23° C., no odour after 24 hours. In enclosed packs at 40° C. for 7 days, an unpleasant odour in head space but not strong. | | |
| Oxygen Barrier: | <0.75 cc/m$^2$/24 hr/atm at 23° C., 75% rh | | |
| Chemical Resistance: | No detectable change in material when exposed to a mixture of hydrogen sulphide gas, water and dilute hydrochloric acid, for 7 days at 40° C. | | |
| Moisture Barrier: | <3 g/m$^2$/24 hrs at 38° C., 90% rh | | |
| Trial Status Property Claim: | All properties are indicative values and should not be taken as limiting specifications | | |

Whilst the above has been given by way of illustrative example of the present invention many variations and modifications thereto will be apparent to those skilled in the art without departing from the broad ambit and scope of the invention as herein set forth in the following claims.

The invention claimed is:

1. A body containment device for storing a deceased body, comprising:

a substantially elongate upper impervious flexible panel member and a substantially elongate lower impervious flexible panel member;

the upper and lower panel members being arranged in a facing relationship and each having an inside surface, an outside surface, opposed side edges and opposed ends, respective side edges of the upper and lower panel members being sealingly joined together or formed integrally therealong, the upper and lower panel members being movable relative to each other to form a cavity between their inside surfaces, the opposed ends forming respective ends of the device with at least one of the ends being openable so that the deceased body can be inserted through the at least one open end into the cavity for storage;

a sealing arrangement for sealingly closing the at least one open end by application of heat and/or pressure thereto, whereby the cavity is hermetically sealed;

a fluid absorbent composition on the inside surface of said lower panel member for absorbing at least some of said gaseous and/or liquid decomposition products escaping from said body; and at least one pressure release means arranged through an aperture in said upper panel member for releasing pressure in the cavity when the pressure due to the gaseous and/or liquid decomposition products in the cavity exceeds a predetermined level, said at least one pressure release means having a first housing member configured with a first chamber therein and a second housing member configured with a second chamber therein, said first housing member being arranged within the cavity and said second housing member being arranged on said outside surface of the upper panel member, a pressure sensitive valve member being positioned between the first and second chambers and is arranged to open to allow the gaseous decomposition products to pass into the second chamber and through vents in said second housing member to atmosphere and thereby releasing pressure in the cavity when the pressure therein exceeds said predetermined level, said first chamber containing vapor retention media for substantially retaining vapor entrained in the gaseous decomposition products passing therethrough and said second chamber containing bacteria filtering media for substantially filtering bacteria before the filtered gaseous decomposition products passing through said vents.

2. The device according to claim 1, wherein the at least one pressure release means is connected to evacuation means for evacuating air within the cavity following sealing thereof.

3. The device according to claim 2, wherein the valve member is housed within a collar extending from said first housing member and the collar is connected to said evacuation means, said second housing member being configured for removably securing to said collar and is removable therefrom to provide access for connecting the evacuation means to the collar for evacuating the cavity.

4. The device according to claim 1, further comprising air conditioning media in one or both of said first and second chambers.

5. The device according to claim 4, wherein said air conditioning media include petroleum based activated carbon and/or fibre based activated carbon.

6. The device according to claim 5, wherein the air conditioning media further include sodium polyacrylate.

7. The device according to claim 6, wherein said petroleum based activated carbon and/or fibre based activated carbon, and sodium polyacrylate, where included, being arranged in layers or a mixed mass.

8. The device according to claim 7, wherein the petroleum based activated carbon is in the form of a layer between 20 to 40 mm, and the fibre based activated carbon is in the form of a layer between 20 to 40 mm, and sodium polyacrylate, where included, is in the form of a layer between 5 to 15 mm.

9. The device according to claim 1, wherein said opposed side edges form respective sides of the device and further comprising one or more hand grips along each of the sides.

10. The device according to claim 9, wherein the handgrips are each reinforced with a PVC tubing.

11. The device according to claim 10, wherein each said handgrip is in the form of a cutout section in one of said side edges and the PVC tubing is fixed in said cutout.

12. The device according to claim 1, wherein each of said upper and lower panel members is formed by lamination or co-extrusion of one or more layers of material or materials.

13. The device according to claim 12, wherein each of said upper and lower panel members has at least one layer of an impervious metallic film and at least one layer of a polymeric material.

14. The device according to claim 13, wherein each of said upper and lower panel members has at least two layers of a polymeric material and is arranged so that the at least one layer of a metallic film is between an outer one and an inner one of the layers of a polymeric material.

15. The device according to claim 14, wherein said outer layer is arranged so as to be relatively more tear and/or puncture resistant than said inner layer.

16. The device according to claim 15, wherein the polymeric material for said outer layer is nylon or polycarbonate, and the polymeric material for said inner layer is polyethylene.

17. The device according to claim 13, wherein said one or more layers of material or materials include at least one layer of ethylene vinyl alcohol bonded to the or each of said at least one layer of a metallic film.

18. The device according to claim 13, wherein the at least one layer of a metallic film may be an aluminium foil.

19. The device according to claim 13, wherein at least the panel member or the layer of the panel member having said inside surface, is formed of a heat weldable material so that an application of heat within a predetermined range of temperature forms a weld joint between the panel members and thereby sealing the cavity.

20. The device according to claim 1, wherein the sealing arrangement is in the form of a heat and/or pressure sealable material arranged on the inside surface of one or each of the upper and lower panel members in a position at or adjacent to said at least one open end.

21. The device according to claim 20, wherein the pressure sealable material is a strip of silicon.

22. The device according to claim 20, wherein the heat sealable material is a strip of heat weldable material.

23. The device according to claim 1, further comprising the at least one pressure release means including one or more gas evacuation means provided for evacuating gases in the cavity following sealing of the at least one opening.

24. The device according to claim 1, wherein the at least one pressure release means is arranged to evacuate gases and to release pressure when pressure inside the cavity exceeds said predetermined level.

25. The device according to claim 1, wherein said absorbent composition is arranged on the inside surface of said lower panel member or contained in one or more packages arranged on the inside surface of said lower panel member.

26. The device according to claim 25, wherein the absorbent composition arranged on the insider surface of said lower panel member or contained in the one or more packages being covered with a pliable perforated sheet attached to said inside surface.

27. The device according to claim 26, wherein said perforated sheet is formed of a polymeric material.

28. The device according to claim 1, wherein the fluid absorbent composition includes one or more liquid absorbent materials arranged for absorbing liquid decomposition products from said body.

29. The device according to claim 28, wherein said one or more liquid absorbent materials are selected from any one or more of silica gel, calcium chloride and sodium polyacrylate.

30. The device according to claim 28, wherein said fluid absorbent composition includes a mixture of silica gel, calcium chloride and sodium polyacrylate, the silica gel being up to 30 %, the calcium chloride up to 8 % and the sodium polyacrylate up to 80%.

31. The device according to claim 1, wherein the fluid absorbent composition includes one or more gaseous absorbent materials arranged for absorbing gaseous decomposition products.

32. The device according to claim 31, wherein said one or more gaseous absorbent materials contains activated carbon.

33. The device according to claim 1, wherein said vapour retention media are in the form of a mixture of clay and calcium chloride and the retention mixture is arranged to provide a retention capacity of between 15% to 35% by weight.

34. The device according to claim 33, wherein the retention mixture has a mesh size of 8 ×12 mesh (approximately 1.5-2.6 mm) and a pore size of 10 Angstrom ($10 \times 10^{-10}$ mm).

35. The device according to claim 1, wherein the bacteria filter is arranged to filter out the majority of known bacteria in decomposing body remains so as to make the treated air that is released back into the environment substantially non hazardous.

36. The device according to claim 1, wherein the bacteria filter media is in the form of a mixture of paper fibers and glass fibers and is manufactured to a weight of approximately 80 grams/meter 5.

37. The device according to claim 1, wherein the bacteria filter media is arranged in a concertina shape to increase filter capacity per unit area.

38. The device according to claim 1, wherein the bacteria filter media has at least one flat circular shaped bacterial filter element.

39. The device according to claim 1, in a body containment system including a plurality of said containment devices formed as a linear array, the array being arranged so that the devices are folded into a stack or rollable into a roll, and the devices being separable along joints between adjacent devices, and further comprising heating and/or pressure means that have spaced heating and/or pressure elements having a length which is equal to or greater than the width between the opposed side edges of the containment devices, at least one of the heating and/or pressure elements being movable towards the other heating and/or pressure element, so that a containment device is separable from the stack or roll, and placed with said at least one openable end thereof between the heating and/or pressure elements and the sealing arrangement in alignment therewith, the movable heating and/or pressure element is then movable towards the other heating and/or pressure element so that the separated containment device is in contact with the heating and/or pressure elements and the sealing arrangement is being heated and/or pressured by the heating and/or pressure elements, whereby the heat and/or pressure applied causes the sealing arrangement to form a weld joint and thereby sealing the cavity, the movable heating and/or pressure element is then moved so as to release the separated containment device from the heating and/or pressure means.

* * * * *

UNITED STATES PATENT AND TRADEMARK OFFICE
CERTIFICATE OF CORRECTION

PATENT NO. : 7,496,995 B2  Page 1 of 1
APPLICATION NO. : 11/455290
DATED : March 3, 2009
INVENTOR(S) : Rosario et al.

It is certified that error appears in the above-identified patent and that said Letters Patent is hereby corrected as shown below:

On the Title page, left column:
"(76) Inventors: Rosario Adamo, Queensland (AU);" should be replaced with
--(76) Inventors: Adamo Rosario, Queensland (AU);--

Signed and Sealed this

Twenty-second Day of June, 2010

David J. Kappos
*Director of the United States Patent and Trademark Office*